(12) United States Patent
Mathews

(10) Patent No.: US 8,127,610 B2
(45) Date of Patent: Mar. 6, 2012

(54) COMPENSATING FOR TEMPERATURE EFFECTS IN A HEALTH MONITORING SYSTEM

(75) Inventor: V. John Mathews, Salt Lake City, UT (US)

(73) Assignee: The Boeing Company, Chicago, IL (US)

( * ) Notice: Subject to any disclaimer, the term of this patent is extended or adjusted under 35 U.S.C. 154(b) by 414 days.

(21) Appl. No.: 12/189,293

(22) Filed: Aug. 11, 2008

(65) Prior Publication Data

US 2010/0031749 A1 Feb. 11, 2010

(51) Int. Cl.
*G01N 29/04* (2006.01)
*G01K 15/00* (2006.01)

(52) U.S. Cl. ........... 73/588; 73/152.12; 73/602; 73/708; 374/1; 374/132

(58) Field of Classification Search .............. 73/588, 73/602, 703, 708; 374/117, 119; 702/34, 702/39
See application file for complete search history.

(56) References Cited

U.S. PATENT DOCUMENTS

| | | | | |
|---|---|---|---|---|
| 6,958,686 B2 * | 10/2005 | Okubo | ............... | 340/447 |
| 7,000,478 B1 * | 2/2006 | Zwollo et al. | ............... | 73/708 |
| 7,061,229 B2 * | 6/2006 | Townsend et al. | ....... | 324/207.12 |
| 7,498,576 B2 * | 3/2009 | Micko | ............... | 250/338.4 |
| 7,726,875 B2 * | 6/2010 | Yuhas | ............... | 374/119 |
| 2009/0306907 A1 | 12/2009 | Ihn et al. | | |

OTHER PUBLICATIONS

Croxford, A.J., Wilcox, P.D., Konstantinidis, G., and Drinkwater, B.W., "Strategies for Overcoming the Effects of Temperature on Guided Wave Structural Health Monitoring", in Proceedings of the SPIE Conference on Health Monitoring and Smart Nondestructive Evaluation of Structural and Biological Systems III (Kundu, T., ed.), vol. 6532, pp. 65321T-1-10, SPIE, 2007.

* cited by examiner

*Primary Examiner* — Jacques M Saint Surin
(74) *Attorney, Agent, or Firm* — Yee & Associates, P.C.

(57) ABSTRACT

A method is present for monitoring a structure. A plurality of modes is identified for a first response for the structure at a first temperature. Each mode in the plurality of modes is adjusted from the first temperature to the second temperature to form a plurality of temperature adjusted modes. A temperature adjusted response is formed from the plurality of temperature adjusted modes in which the temperature adjusted response is adjusted to a second temperature from the first temperature. The temperature adjusted response is compared to a second response to evaluate the changes in the structure between the two sets of measurements.

23 Claims, 10 Drawing Sheets

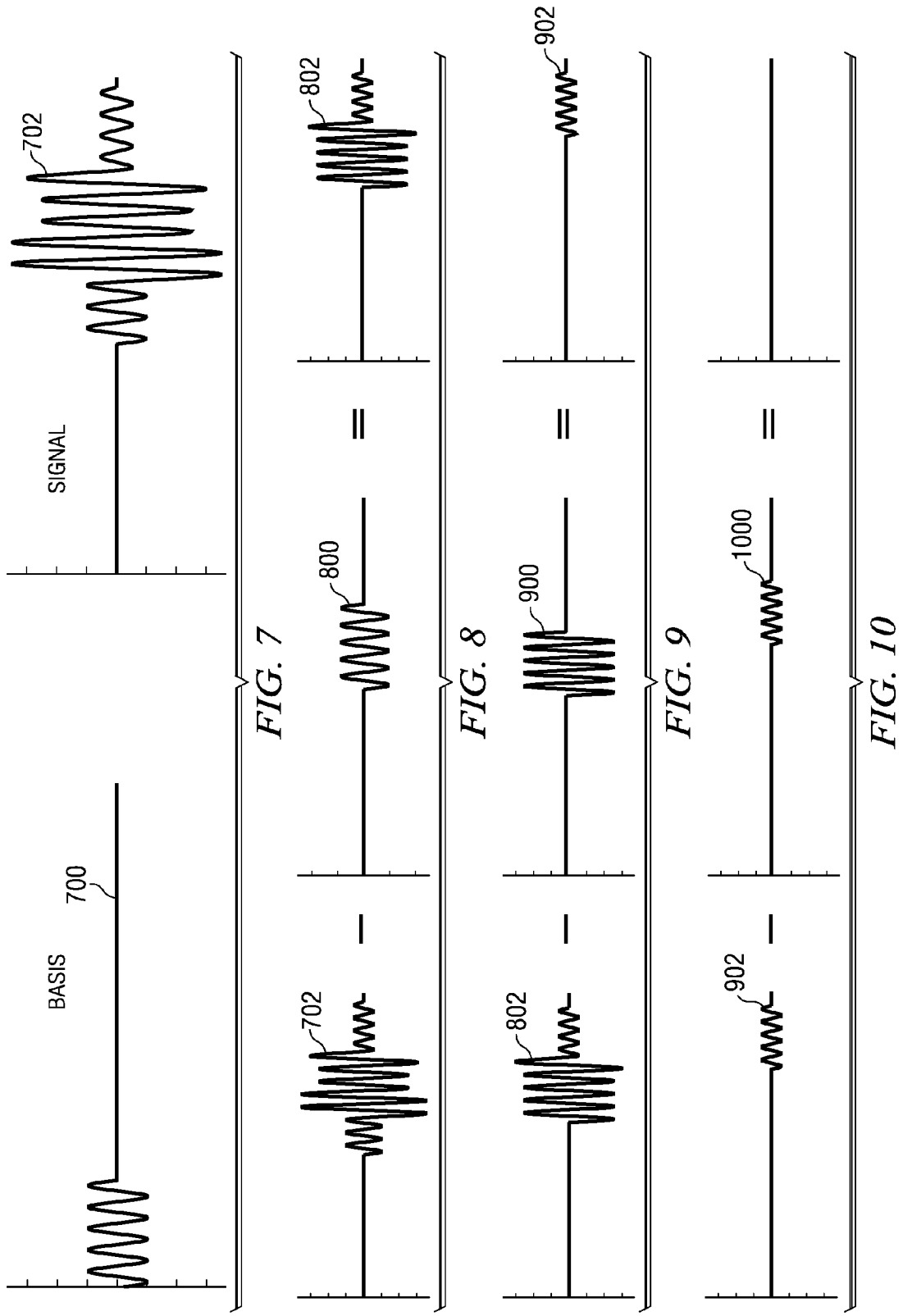

COMPENSATING FOR TEMPERATURE EFFECTS IN A HEALTH MONITORING SYSTEM

BACKGROUND INFORMATION

1. Field

The present disclosure relates generally to processing data and in particular to processing data from responses of a structure to an input wave form. Still more particularly, the present disclosure relates to a method, apparatus, and computer usable program code for identifying anomalies in a structure.

2. Background

Composite and metallic aircraft structures may be susceptible to internal changes that may occur from fatigue, impacts, and other events or conditions. Composite materials typically have a minimal visual indication of these types of changes. As a result, an aircraft may be inspected to assess the integrity of the structure on a periodic basis, or after visual indications of surface anomalies, such as dent and scratch.

For example, impacts to a structure, such as an aircraft, may occur during cargo loading and unloading. Inspections of the structure of an aircraft may be time consuming and costly in terms of the time and skill needed to perform the inspection. Further, an airline may incur lost revenues from the aircraft being out of service.

Health monitoring techniques have been developed and used to monitor structures and their components. These techniques often build the health monitoring systems into the structures. These health monitoring systems may be used to determine whether changes have occurred to these structures over time.

Sudden changes in environments, such as electromagnetic effects, mechanical stresses, and other environmental effects may affect the integrity of various materials and structures over time. By having health monitoring systems built into or associated with the structures to monitor the structures during use, appropriate measures and responses may be taken to prevent catastrophic failures and may prolong the life span of these structures.

The monitoring of structures may include various non-destructive evaluation methods, such as ultrasonic testing or x-ray testing. Ultrasonic testing uses contact-based transducers to mechanically scan a structure. These distributed sensors and actuators may be surface mounted on the structure or may be embedded in the structure to generate and propagate control of diagnostic signals into the structure being monitored.

A structural health monitoring system is based on using a transmitter and a sensor configuration to transmit waveforms at various frequency ranges and acquire data from the responses. Often times, transducers may function both as a transmitter and a sensor. Although structural health monitoring systems may provide an automated on board system for detecting and characterizing anomalies or changes that may require maintenance, these types of systems may provide for false indications that further inspection and/or maintenance may be needed.

These health monitoring systems may have inaccuracies caused by environmental conditions and/or components within the health monitoring system. For example, changes in temperature may affect the results generated by the health monitoring system.

Therefore, it would be advantageous to have a method and apparatus that overcomes the problems described above.

SUMMARY

In one advantageous embodiment, a method is present for monitoring a structure. A plurality of modes is identified for a first response for the structure at a first temperature. Each mode in the plurality of modes is adjusted from the first temperature to the second temperature to form a plurality of temperature adjusted modes. A temperature adjusted response is formed from the plurality of temperature adjusted modes in which the temperature adjusted response is adjusted to a second temperature from the first temperature. The temperature adjusted response is compared to a second response obtained at the second temperature.

In another advantageous embodiment, an apparatus comprises a structure having a set of components, a set of transmitters, a set of sensors, and a data processing system. The set of transmitters is physically associated with the set of components, wherein the set of transmitters is capable of sending signals into the set of components. The set of sensors is physically associated with the set of components, wherein the set of sensors is capable of detecting a response to the signals. The data processing system is in communication with the set of transmitters and the set of sensors. The data processing system is capable of identifying a plurality of modes for a first response for the structure at a first temperature, adjusting each mode in the plurality of modes from the first temperature to a second temperature to form a plurality of temperature adjusted modes, forming a temperature adjusted response from the plurality of temperature adjusted modes in which the temperature adjusted response is adjusted to the second temperature from the first temperature, and comparing the temperature adjusted response to a second response obtained at the second temperature.

In yet another advantageous embodiment, a computer program product comprises a computer recordable storage media and program code. Program code is present for identifying a plurality of modes for a first response for a structure at a first temperature. Program code is also present for adjusting each mode in the plurality of modes from the first temperature to a second temperature to form a plurality of temperature adjusted modes. Program code is present for forming a temperature adjusted response from the plurality of temperature adjusted modes in which the temperature adjusted response is adjusted to the second temperature from the first temperature. Also, program code is present for comparing the temperature adjusted response to a second response obtained at the second temperature.

The features, functions, and advantages can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the advantageous embodiments are set forth in the appended claims. The advantageous embodiments, however, as well as a preferred mode of use, further objectives and advantages thereof, will best be understood by reference to the following detailed description of an advantageous embodiment of the present disclosure when read in conjunction with the accompanying drawings, wherein:

FIGS. 7-10 are diagrams illustrating the decomposing of a reference signal in accordance with advantageous embodiments;

DETAILED DESCRIPTION

Figure 1:
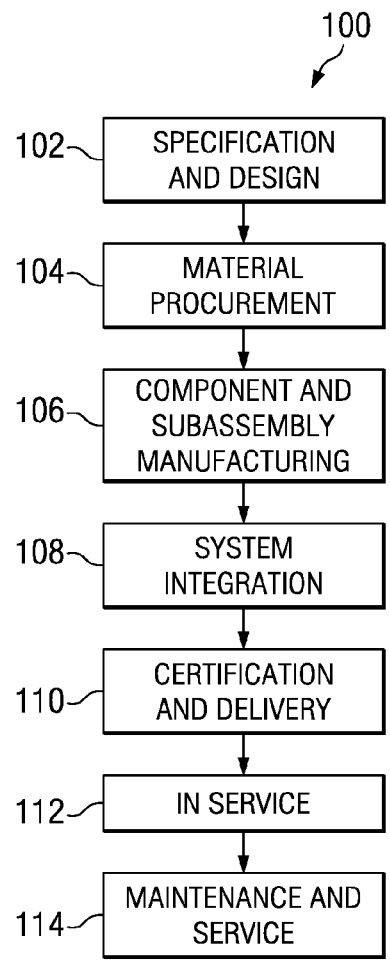
FIG. 1 is a diagram illustrating an aircraft manufacturing and service method in which an advantageous embodiment may be implemented.
Figure 2:
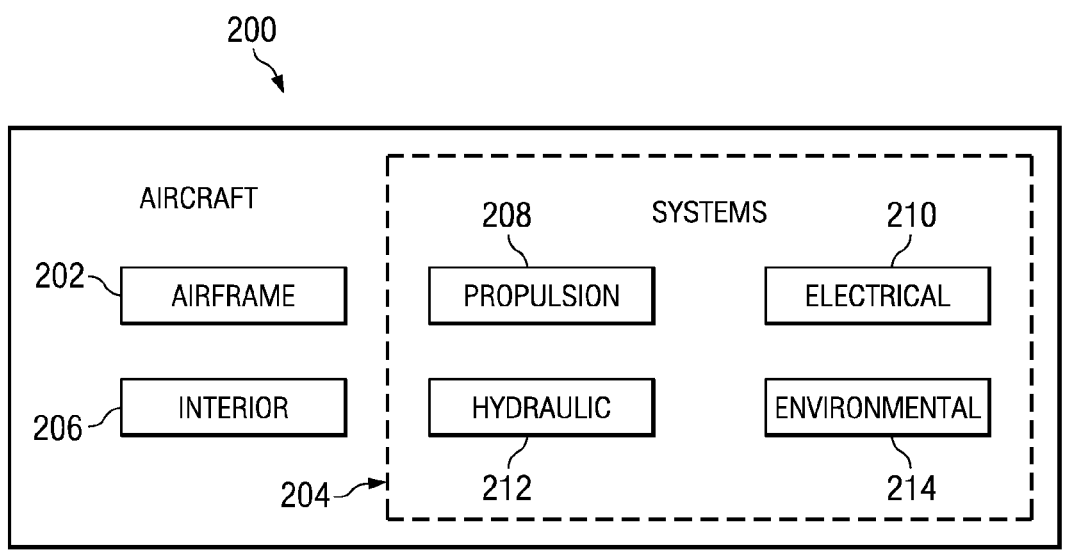
FIG. 2 is a diagram of an aircraft in accordance with an advantageous embodiment.

Referring more particularly to the drawings, embodiments of the disclosure may be described in the context of the aircraft manufacturing and service method 100 as shown in FIG. 1 and aircraft 200 as shown in FIG. 2. Turning first to FIG. 1, a diagram illustrating an aircraft manufacturing and service method is depicted in accordance with an advantageous embodiment. During pre-production, exemplary aircraft manufacturing and service method 100 may include specification and design 102 of aircraft 200 in FIG. 2 and material procurement 104.

During production, component and subassembly manufacturing 106 and system integration 108 of aircraft 200 in FIG. 2 takes place. Thereafter, aircraft 200 in FIG. 2 may go through certification and delivery 110 in order to be placed in service 112. While in service by a customer, aircraft 200 in FIG. 2 is scheduled for routine maintenance and service 114, which may include modification, reconfiguration, refurbishment, and other maintenance or service.

Each of the processes of aircraft manufacturing and service method 100 may be performed or carried out by a system integrator, a third party, and/or an operator. In these examples, the operator may be a customer. For the purposes of this description, a system integrator may include, without limitation, any number of aircraft manufacturers and major-system subcontractors; a third party may include, without limitation, any number of venders, subcontractors, and suppliers; and an operator may be an airline, leasing company, military entity, service organization, and so on.

With reference now to FIG. 2, a diagram of an aircraft is depicted in which an advantageous embodiment may be implemented. In this example, aircraft 200 is produced by aircraft manufacturing and service method 100 in FIG. 1 and may include airframe 202 with a plurality of systems 204 and interior 206. Examples of systems 204 include one or more of propulsion system 208, electrical system 210, hydraulic system 212, and environmental system 214. Any number of other systems may be included. Although an aerospace example is shown, different advantageous embodiments may be applied to other industries, such as the automotive industry.

Apparatus and methods embodied herein may be employed during any one or more of the stages of aircraft manufacturing and service method 100 in FIG. 1. For example, components or subassemblies produced in component and subassembly manufacturing 106 in FIG. 1 may be fabricated or manufactured in a manner similar to components or subassemblies produced while aircraft 200 is in service 112 in FIG. 1.

Also, one or more apparatus embodiments, method embodiments, or a combination thereof may be utilized during production stages, such as component and subassembly manufacturing 106 and system integration 108 in FIG. 1, for example, without limitation, by substantially expediting the assembly of or reducing the cost of aircraft 200. Similarly, one or more of apparatus embodiments, method embodiments, or a combination thereof may be utilized while aircraft 200 is in service 112 or during maintenance and service 114 in FIG. 1.

In one illustrative example, health monitoring systems of the advantageous embodiments may be implemented during component and subassembly manufacturing 106 in system integration 108. In other advantageous embodiments, health monitoring systems may be added or implemented during maintenance and service 114. In these different advantageous embodiments, these health monitoring systems may include methods and apparatus for identifying anomalies in a structure in which dissimilarity indices are identified during monitoring.

Figure 3:
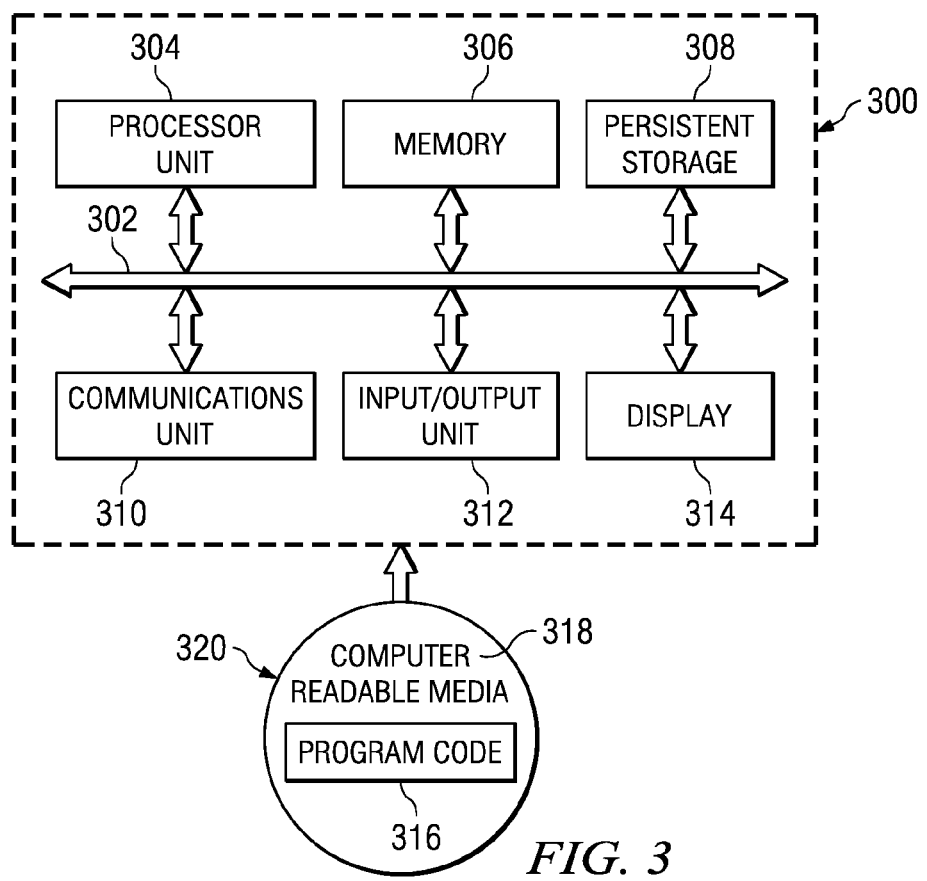
FIG. 3 is a diagram of a data processing system in accordance with an advantageous embodiment.

Turning now to FIG. 3, a diagram of a data processing system is depicted in accordance with an advantageous embodiment. In these examples, data processing system 300 may implement processes to identify dissimilarity indices in accordance with advantageous embodiments. These dissimilarity indices may be used to determine whether an anomaly or change is present in a structure. In this illustrative example, data processing system 300 includes communications fabric 302, which provides communications between processor unit 304, memory 306, persistent storage 308, communications unit 310, input/output (I/O) unit 312, and display 314.

Processor unit 304 serves to execute instructions for software that may be loaded into memory 306. Processor unit 304 may be a set of one or more processors or may be a multiprocessor core, depending on the particular implementation. Further, processor unit 304 may be implemented using one or more heterogeneous processor systems in which a main processor is present with secondary processors on a single chip. As another illustrative example, processor unit 304 may be a symmetric multi-processor system containing multiple processors of the same type.

Memory 306 and persistent storage 308 are examples of storage devices. A storage device is any piece of hardware that is capable of storing information either on a temporary basis and/or a permanent basis. Memory 306, in these examples, may be, for example, a random access memory or any other suitable volatile or non-volatile storage device.

Persistent storage 308 may take various forms depending on the particular implementation. For example, persistent storage 308 may contain one or more components or devices. For example, persistent storage 308 may be a hard drive, a flash memory, a rewritable optical disk, a rewritable magnetic tape, or some combination of the above. The media used by persistent storage 308 also may be removable. For example, a removable hard drive may be used for persistent storage 308.

Communications unit 310, in these examples, provides for communications with other data processing systems or devices. In these examples, communications unit 310 is a network interface card. Communications unit 310 may provide communications through the use of either or both physical and wireless communications links.

Input/output unit 312 allows for input and output of data with other devices that may be connected to data processing system 300. For example, input/output unit 312 may provide a connection for user input through a keyboard and mouse. Further, input/output unit 312 may send output to a printer. Display 314 provides a mechanism to display information to a user.

Instructions for the operating system and applications or programs are located on persistent storage 308. These instructions may be loaded into memory 306 for execution by processor unit 304. The processes of the different embodiments may be performed by processor unit 304 using computer implemented instructions, which may be located in a memory, such as memory 306.

These instructions are referred to as program code, computer usable program code, or computer readable program code that may be read and executed by a processor in processor unit 304. The program code in the different embodiments may be embodied on different physical or tangible computer readable media, such as memory 306 or persistent storage 308.

Program code 316 is located in a functional form on computer readable media 318 that is selectively removable and may be loaded onto or transferred to data processing system 300 for execution by processor unit 304. Program code 316 and computer readable media 318 form computer program product 320 in these examples.

In one example, computer readable media 318 may be in a tangible form, such as, for example, an optical or magnetic disc that is inserted or placed into a drive or other device that is part of persistent storage 308 for transfer onto a storage device, such as a hard drive that is part of persistent storage 308.

In a tangible form, computer readable media 318 also may take the form of a persistent storage, such as a hard drive, a thumb drive, or a flash memory that is connected to data processing system 300. The tangible form of computer readable media 318 is also referred to as computer recordable storage media. In some instances, computer readable media 318 may not be removable.

Alternatively, program code 316 may be transferred to data processing system 300 from computer readable media 318 through a communications link to communications unit 310 and/or through a connection to input/output unit 312. The communications link and/or the connection may be physical or wireless in the illustrative examples. The computer readable media also may take the form of non-tangible media, such as communications links or wireless transmissions containing the program code.

The different components illustrated for data processing system 300 are not meant to provide architectural limitations to the manner in which different embodiments may be implemented. The different illustrative embodiments may be implemented in a data processing system including components in addition to or in place of those illustrated for data processing system 300. Other components shown in FIG. 3 can be varied from the illustrative examples shown.

As one example, a storage device in data processing system 300 is any hardware apparatus that may store data. Memory 306, persistent storage 308, and computer readable media 318 are examples of storage devices in a tangible form.

In another example, a bus system may be used to implement communications fabric 302 and may be comprised of one or more buses, such as a system bus, or an input/output bus. Of course, the bus system may be implemented using any suitable type of architecture that provides for a transfer of data between different components or devices attached to the bus system.

Additionally, communications unit 310 may include one or more devices used to transmit and receive data, such as a modem or a network adapter. Further, a memory may be, for example, memory 306 or a cache such as found in an interface and memory controller hub that may be present in communications fabric 302.

The different advantageous embodiments recognize that changes to a structure may be characterized using differences between baseline signals and test signals associated with a transmitter and sensor pair associated with a structural health monitoring system. The signals acquired when the structure is known to be healthy or intact without changes are referred to as baseline signals.

Of course, baseline signals also may be signals at some selected state of the structure in which some changes may be present. These types of baselines signals may be obtained to determine whether additional changes have occurred in a structure. The signals acquired during inspections are referred to as test signals. These types of signals may be referred to generally as responses.

In other words, baseline signals and test signals are both types of responses that are generated when a signal is sent into a structure. Changes in the structure are detected and characterized using differences between baseline signals and test signals.

The different advantageous embodiments recognize that in addition to changes that may be present in the structure, environmental factors such as, for example, temperature changes, load differences, and/or debris located on the structure may introduce variations into the test signals that would not be present. The different advantageous embodiments recognize that temperature changes may affect the accuracy of results obtained by comparing baseline signals to test signals.

If temperature changes are not compensated for or taken into account, the comparison of a baseline signal to a test signal may incorrectly indicate that changes in the structure are present. The different advantageous embodiments recognize that one manner in which temperature changes may be taken into account is to collect baseline data at all temperatures of interest.

This set of baseline data may then be used in the comparisons at a later time. The different advantageous embodiments also recognize that another possible solution is to perform a transform on the test signal to transform the signal into one in which the temperature is that of the baseline signal.

The different advantageous embodiments recognize, however, collecting baseline data at the different temperatures of interest may be impractical for many aircraft systems. This lack of practicality may occur because, in most cases, propagation characteristics of different aircraft built using the same design may be different enough that baseline data must be collected for each aircraft separately. Although this type of process may be straightforward, performing data collection for the desired temperature ranges for every aircraft is expensive and time consuming.

Further, the different advantageous embodiments recognize that the different components of a waveform are not affected by temperature variations in an identical manner. A component in a waveform may also be referred to as a mode. The different advantageous embodiments recognize that adjusting the entire waveform with a single transform may not provide results that are as accurate as desired.

Thus, the different advantageous embodiments treat different components of signals, such as the physical modes of wave propagation, individually and differently from each other. A mode is one type of physical propagation in these examples. The different advantageous embodiments provide a method and apparatus for compensating or adjusting for the temperature differences when comparing responses. A plurality of modes is identified for a first response in the structure at a first temperature. Each mode in the plurality of modes is adjusted from the first temperature to the second temperature to form a plurality of temperature adjusted modes.

A temperature adjusted response is formed from the plurality of temperature adjusted modes in which the temperature adjusted response is adjusted to the second temperature from the first temperature. The temperature adjusted response is compared to a second response obtained at the second temperature. In these examples, the temperature adjusted response may be either the baseline signal or the test signal.

Figure 4:
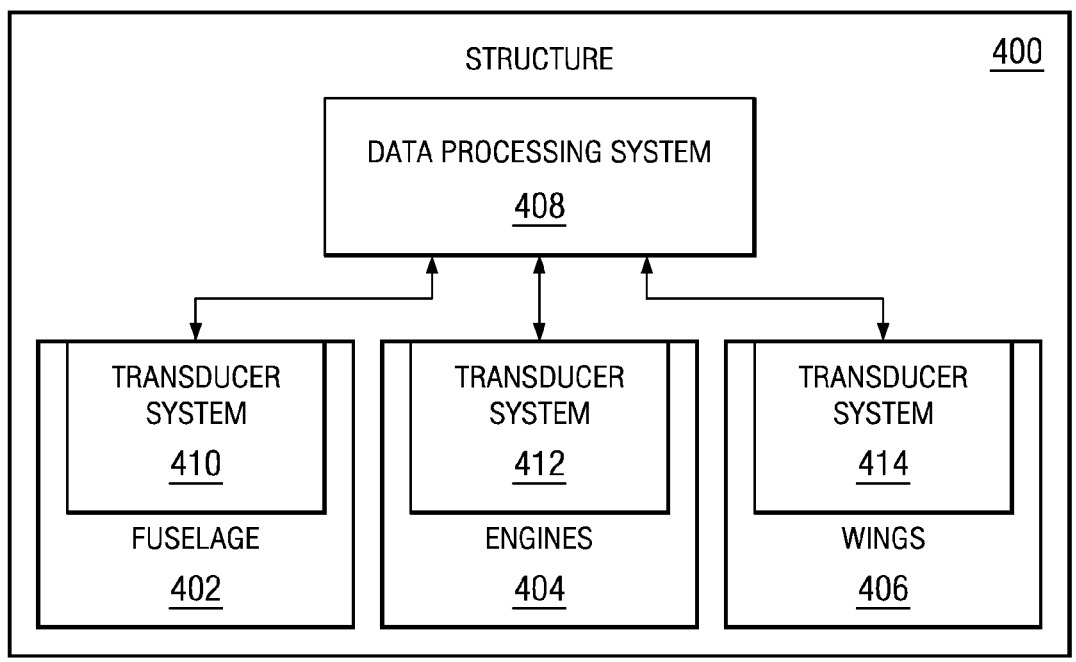
FIG. 4 is a diagram illustrating components used for structural health monitoring in a structure in accordance with an advantageous embodiment.

Turning now to FIG. 4, a diagram illustrating components used for structural health monitoring in a structure is depicted in accordance with an advantageous embodiment. Structure 400 is an example of a structure in which a health monitoring system may be implemented. Structure 400 may take many forms, such as an aircraft, a car, a tank, a ship, a submarine, a spacecraft, a dam, a building, a bridge, or some other suitable structure.

In this example, structure 400 takes the form of an aircraft. Structure 400 includes fuselage 402, engines 404, and wings 406. Other components also may be found in structure 400, but only these depicted ones are presented for purposes of illustrating different features in the different advantageous embodiments.

Structure 400 also includes data processing system 408, transducer system 410, transducer system 412, and transducer system 414. In these examples, data processing system 408, transducer system 410, transducer system 412, and transducer system 414 form a structural health monitoring system. Although transducers are used for transmitters and sensors, in these examples, any type of transmitter, sensor, or device that is capable of sending and detecting signals at the frequencies needed to transmit the signals into a material may be used.

Data processing system 408 may be implemented in structure 400 using a data processing system, such as data processing system 300 in FIG. 3. Data processing system 408 may take the form of software, hardware, or a combination of software and hardware. In this example, data processing system 408 is implemented in software using a data processing system, such as data processing system 300 in FIG. 3.

Transducer systems 410, 412, and 414 are examples of transmitters and sensors that may be implemented in structure 400 to transmit signals and detect responses to those signals. In these examples, the transducers in these systems are "associated" with the particular components in structure 400.

A transmitter or sensor, such as those in transducer systems 410, 412, and 414, may be physically associated with the component by being attached to the component or even embedded within the component. In these examples, the transducers are fixed transmitters and fixed sensors that are not moved once they are placed. In particular, these transducers may perform or function both as a transmitter and a sensor.

In this depicted example, transducer system 410 is a set of one or more transducers that is placed onto or within fuselage 402. Transducer system 410 may be attached to surfaces within fuselage 402 or may be embedded into the materials itself, depending on the particular implementation.

The different transducers within transducer system 410 are arranged to be capable of monitoring one or more areas within fuselage 402. These areas may be selected based on different factors, such as identifying areas in which damage may cause a failure within fuselage 402. In a similar fashion, transducer system 412 is attached to or integrated with components in engines 404. Transducer system 414 also is integrated and configured to collect data from one or more areas in wings 406.

Transducer systems 410, 412, and 414 are controlled by data processing system 408. Data processing system 408 may send signals for transmission by these transducer systems. Further, the responses received from transmitting these signals are returned to data processing system 408 for processing. The responses collected from transducer systems 410, 412, and 414 are compared to baseline or comparison signals.

The illustration of structure 400 in FIG. 4 is presented for the purposes of explaining one advantageous embodiment. This illustration is not meant to limit the manner in which different advantageous embodiments may be implemented or embodied. For example, in other advantageous embodiments, other numbers of transducer systems may be present. For example, structure 400 may include five, ten, twenty, or some other suitable number of transducer systems depending on the particular implementation. Also, additional structural health monitoring systems, in addition to data processing system 408, also may be present for redundancy.

Figure 5:
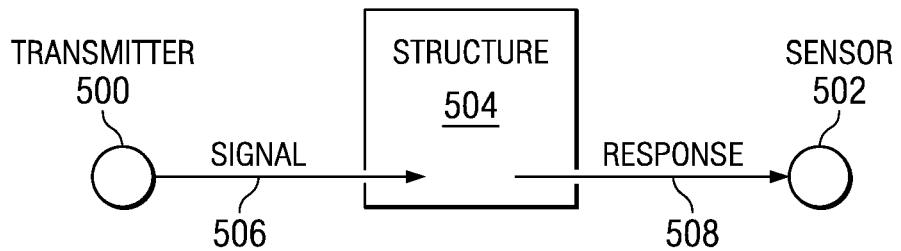
FIG. 5 is a diagram illustrating signal transmission and detection in accordance with an advantageous embodiment.

Turning now to FIG. 5, a diagram illustrating signal transmission and detection is depicted in accordance with an advantageous embodiment. In this example, transmitter 500 and sensor 502 may be used to test structure 504. Transmitter 500 and sensor 502 are an example of a transmitter and sensor that may be found in transducer system 410 in FIG. 4. Structure 504 may be, for example, fuselage 402 or wings 406 in FIG. 4.

Transmitter 500 transmits or sends signal 506 into structure 504. Signal 506 is a waveform having a selected frequency range. Response 508 is detected by sensor 502. Response 508 is generated in response to the transmission of signal 506 into structure 504. Response 508 may be a baseline signal or a test signal depending on the particular time that signal 506 was sent. Although, in this example, sensor 502 is shown as receiving response 508 on an opposite side of structure 504 from transmitter 500, sensor 502 may be located on the same side of structure 504 as transmitter 500. With this configuration, response 508 is detected from reflections or scattering of signal 506 being transmitted into structure 504. In other examples, sensor 502 may be the same transducer that transmitted signal 506.

Response 508 is used, in these different illustrative examples, in a comparison with a prior response to determine whether changes have occurred in structure 504. These changes may be anomalies that occur through various stresses, sudden impacts and other environmental conditions to which structure 504 is subjected to over time.

Figure 6:
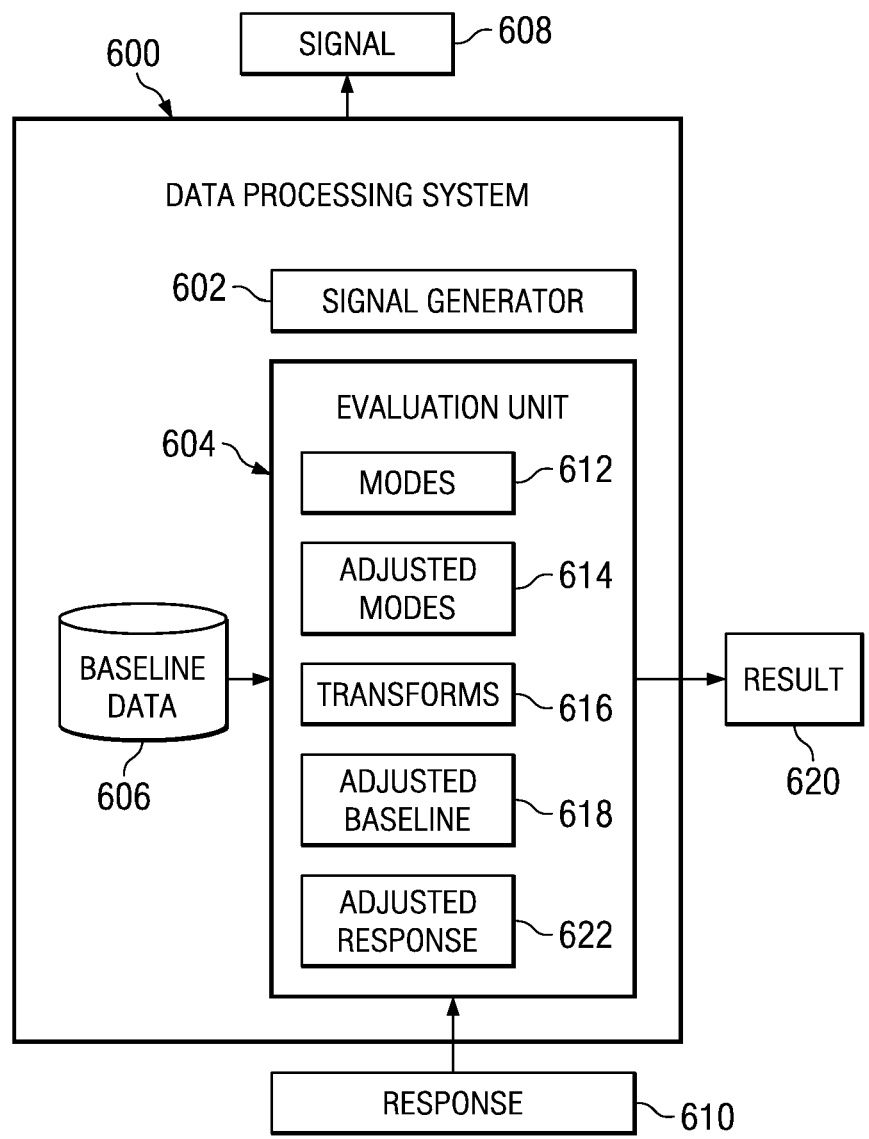
FIG. 6 is a diagram of a data processing system in a structural health monitoring system in accordance with an advantageous embodiment.

With reference now to FIG. 6, a diagram of a data processing system in a structural health monitoring system is depicted in accordance with an advantageous embodiment. In this example, data processing system 600 is an example of one implementation of components in a data processing system such as, for example, data processing system 408 in FIG. 4. As illustrated, data processing system 600 includes signal generator 602, evaluation unit 604, and baseline data 606.

Signal generator 602 generates signal 608 which may be transmitted by a transducer system such as, for example, transducer system 410 in FIG. 4, using a transmitter and sensor such as, for example, transmitter 500 and sensor 502 in FIG. 5. Evaluation unit 604 may receive response 610 from a transducer system. Modes 612 may be identified from a signal in baseline data 606. These modes may then be adjusted by evaluation unit 604 to generate adjusted modes 614. Modes 612 may be adjusted using transforms 616. Each mode within modes 612 may be adjusted by a particular transform within transforms 616 to form adjusted modes 614. These adjusted modes may be recombined into adjusted baseline 618. Adjusted baseline 618 may be compared to response 610.

Baseline data 606 may take the form of signals generated in response to interrogating the structure at a prior point in time. This prior point in time may be a time when the structure was first manufactured. Of course, baseline data 606 may contain signals from other points in time after the creation of the structure. In the different advantageous embodiments, these signals may be for a point in time when the structure is considered to be intact or healthy. When the structure is considered to be intact or healthy, some changes in the structure from its original manufactured state may be present.

Evaluation unit 604 generates result 620 in response to the comparison between adjusted baseline 618 and response 610. Result 620 may take various forms. For example, result 620 may be, for example, an identification as to whether a change has occurred in a map. The map may be, for example, a two-dimensional or three-dimensional map of the structure with an identification of locations where changes may have been detected in the structure.

In other advantageous embodiments, instead of adjusting baseline data 606, response 610 may be adjusted. In this type of embodiment, modes 612 are modes identified for response 610. These modes may be transformed by transforms 616 to form adjusted modes 614 for response 610. Adjusted modes 614 may then be recombined to form adjusted response 622. Adjusted response 622 may be compared to a signal in baseline data 606 to generate result 620 in this type of implementation.

In the illustrative examples, the baseline signal is decomposed into mode components. In other words, a number of modes are identified from the response. In these examples, a wave packet corresponding to a mode of waveform propagation arriving directly at the sensor and another arriving at the sensor after one or more reflections are considered to be distinct modes in this discussion. These wave packets arriving at the sensor are processed individually. The wave packet corresponding to each mode may be obtained by an appropriate transformation of the excitation signal:

$$x_k^{(b)}(n) = \alpha_k x^{(b)}(n-m_k)$$

FIGS. 7-10 provide examples of one manner in which decomposition of a signal may be performed. Of course, other advantageous embodiments may use other techniques or methods. For example, any decompositions that identify physical modes of wave propagation may be used in the different advantageous embodiments. With reference now to FIG. 7, a diagram illustrating the decomposing of a reference signal is depicted in accordance with an advantageous embodiment. In this example, basis signal 700 and reference signal 702 are shown. Basis signal 700 may be scaled and/or shifted to identify different modes within reference signal 702. This scaling and/or shifting may be performed to match or approximate the form of a portion of reference signal 702.

In FIG. 8, basis signal 800 is subtracted from reference signal 702. Basis signal 800 is a scaled and/or shifted version of basis signal 700 and is an example of one mode for reference signal 702. This signal is a simpler signal, as compared to reference signal 702. This subtraction results in signal 802, which is the resulting signal when basis signal 800 has been removed from reference signal 702.

In FIG. 9, basis signal 900 is formed through scaling and/or shifting and is subtracted from signal 802 to form signal 902. Basis signal 900 is another mode for reference signal 702 in these examples. In FIG. 10, basis signal 1000 is formed based on a scaled and/or shifted version of basis signal 700. Basis signal 1000 is subtracted from basis signal 900 with no portion of reference signal 702 remaining. Basis signal 1000 forms a third mode for reference signal 702.

Basis signals 800, 900, and 1000 form the signals for the different modes. These signals may be summed to reform reference signal 702 in FIG. 7. These basis signals may be adjusted and/or transformed to compensate or take into account temperature differences between reference signal 702 in FIG. 7 and the temperature of another signal for which a comparison is to be made. In these examples, each of these modes may be individually adjusted to take into account the type of changes in propagation that may be caused for these modes when temperature differences are present.

In this example, only three modes are illustrated for purposes of depicting one manner in which a decomposition process may occur. In other advantageous embodiments, other modes may be obtained from the reference signal. For example, twenty modes, thirty modes, or some other suitable number of modes may be selected. A similar process may be performed for the comparison signals, as well as the reference signals.

Figure 11:
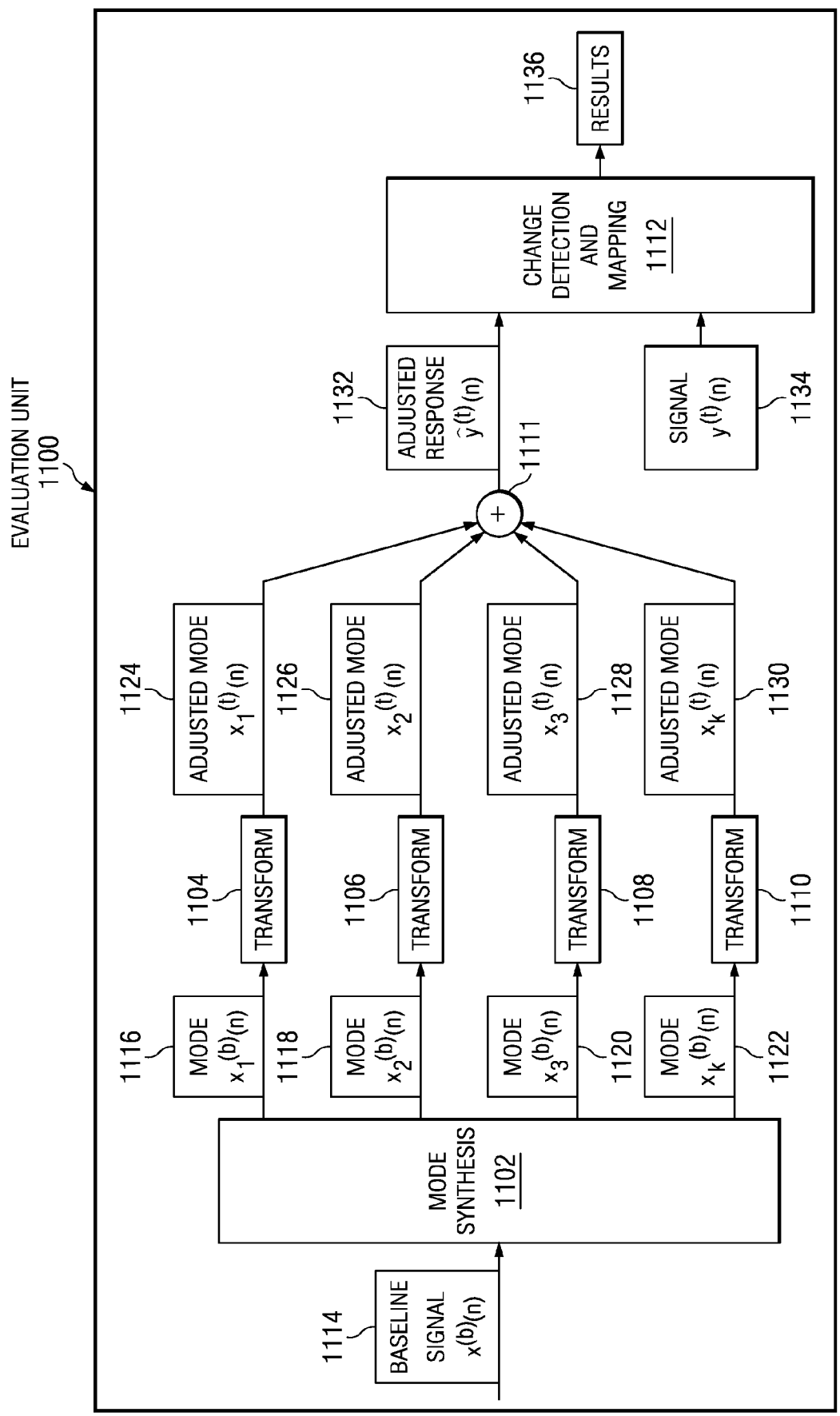
FIG. 11 is a diagram illustrating an evaluation unit in accordance with an advantageous embodiment.

With reference now to FIG. 11, a diagram illustrating an evaluation unit is depicted in accordance with an advantageous embodiment. In this example, evaluation unit 1100 is an example of one implementation for evaluation unit 604 in FIG. 6.

In this example, evaluation unit 1100 includes mode synthesis 1102, transform 1104, transform 1106, transform 1108, transform 1110, summing unit 1111, and change detection and mapping 1112. Mode synthesis 1102 receives signal 1114 and generates modes 1116, 1118, 1120, and 1122. Each of these modes is a physical mode of propagation that is part of signal 1114. In other words, each of these modes is a component of signal 1114. Mode synthesis 1102 may identify modes from signal 1114 using a number of different mechanisms.

For example, a mode may be identified using a shape that is changed to estimate each mode of propagation, such as those illustrated in FIGS. 7-10. In another example, a mode may be identified using a filter bank. The output of each filter in a filter bank may be considered a mode component.

In the embodiments, a transform may be used to decompose or identify modes. In another example, a signal may have many modes, such as the examples in FIGS. 7-10 and the signal may be expressed as follows:

$$s(t) = \sum_{k=1}^{N} a_k x(t - d_k)$$

where x(t) is the excitation signal and s(t) is the signal arriving at one of the sensors. In this equation, (N) represents the number of modes in the decomposition.

The attenuation constants a and the time delays d are estimated for each mode. In one example, the strongest mode may be estimated using a correlation analysis, subtracted by the strongest mode from the received signal, which is referred to as the response. The second strongest mode may be estimated from the residual. This process may be repeated until the desired number of modes has been identified.

In the different advantageous embodiments, each of the modes is transformed individually and separately from the other modes to adjust and/or compensate for the temperature at which signal 1114 was collected to a second temperature for another signal that is to be compared with signal 1114. In these examples, signal 1114 may be a response in the form of a test signal, while the other signal is a response in the form of a baseline signal. In other advantageous embodiments, the baseline signal may be adjusted and compared to the response.

Modes 1116, 1118, 1120, and 1122 are adjusted or processed by transforms 1104, 1106, 1108, and 1110 respectively. In performing transforms, an individual mode may be transformed or adjusted from one temperature to another temperature in a number of different ways.

For example, assume that $y^{(b)}$ (h) and $x^{(b)}$ (n) represent the response received and the excitation signal observed at some baseline temperature. Also, assume that the response is at temperature t is $y^{(t)}$ (n) and the corresponding excitation signal is $x^{(t)}$ (n). A response is made up of several components, each of which may be a wave packet corresponding to a specific mode of wave propagation or a reflected version of such a mode. Thus, the response may be modeled as $$y^{(b)}(n) = \sum_{k=1}^{K} x_k^{(b)}(n) + \eta^{(b)}(n) \quad (1)$$

where $x_k^{(b)}$ (n) is the waveform corresponding to the kth wave packet and K represents the number of wave packets contained in the waveform. In the above expression, $n^{(b)}$ (t) represents noise that is uncorrelated with the individual wave packets. In this equation, $\eta^{(b)}$ (t) represents the noise or error term, b represents the temperature at which the data was acquired for a baseline signal, and t represents the temperature at which data was acquired for the test signal, and k indicates the mode.

Several approaches that may be used to mathematically decompose a waveform into its component basis functions are currently available. The illustrative examples employ a decomposition using the following basis signal:

$$x_k^{(b)}(n) = \alpha_k x^{(b)}(n - m_k) \quad (3)$$

where $x_k^{(b)}$ (n) is a waveform representing the kth mode of propagation, $x^{(b)}$ is the transmitted signal at temperature b, and $\alpha_k$ is a scaling factor that depends, among other factors, on the material properties, characteristics of the structure, and the length of the propagation path. The delay value $m_k$ is not necessarily an integer multiple of the sampling period, but the sampling rate is set to be sufficiently fine such that any error in using an integer approximation is negligibly small.

The effect of temperature on wave propagation is essentially two-fold. First, a change may be present in the shape of the wave packets. Second, the speed of wave propagation changes with temperature. Both these changes are dependent on the mode of wave propagation, such as different modes, and therefore the corresponding wave packets arriving at the sensor exhibit different types of changes in the shape and are subject to different changes to their propagation velocity.

In these examples, the effect of temperature on each wave packet is modeled using a linear, time-invariant filter. In other words, the response at temperature t may be written as $$y^{(t)}(n) = \sum_{k=1}^{K} \left\{ \sum_{i=-N_k}^{N_k} \beta_{k,i} x_k^{(b)}(n-i) \right\} + \eta^{(t)}(n)$$

where $\beta_{k,i}$ corresponds to the coefficients o, the compensation filter associated with the kth wave packet, and the range $[-N_k, N_k]$ is the duration of the impulse response of the linear filter than models the temperature effects on the wave packets. With a training set of data available at the baseline and the temperature of interest, the parameters $\beta_{k,i}$ may be estimated using a least-squares or another appropriate technique.

As a result of the transforms, adjusted modes 1124, 1126, 1128, and 1130 are output from these transforms. These modes are combined at summing unit 1111 to form adjusted response 1132.

In this illustrative example, adjusted response 1132 is the estimate of the signal at temperature t, which is the test temperature in these examples. The test temperature is the temperature at which the test signal is acquired to form the response, such as test signal 1134.

Adjusted response 1132 is compared with test signal 1134 at temperature t by change detection and mapping 1112 to determine whether a change is present in the structure to generate results 1136.

If a change has been detected, the location of the change also may be mapped by change detection and mapping 1112. Results 1136 may be output for use by other systems or components.

In these illustrative examples, instead of decomposing baseline signal 1114, mode synthesis 1102 may decompose signal 1134. In this manner, adjusted response 1132 is an adjusted form of test signal 1134. In this type of example, the adjusted response for signal 1134 may be compared to signal 1114 by the changed detection and mapping 1112 to generate results 1136.

The illustration of evaluation unit 1100 in FIG. 11 has been provided for the purpose of illustrating one manner in which temperature compensations or adjustments may be made. This illustration is not meant to imply architectural or physical limitations to the manner in which different embodiments may be implemented. For example, although only four modes and four transforms are illustrated, other numbers of modes and transforms may be used, depending on the particular implementation. For example, in other implementations 8, 20, 50, or some other suitable number of modes and transforms may be used.

Figure 12:
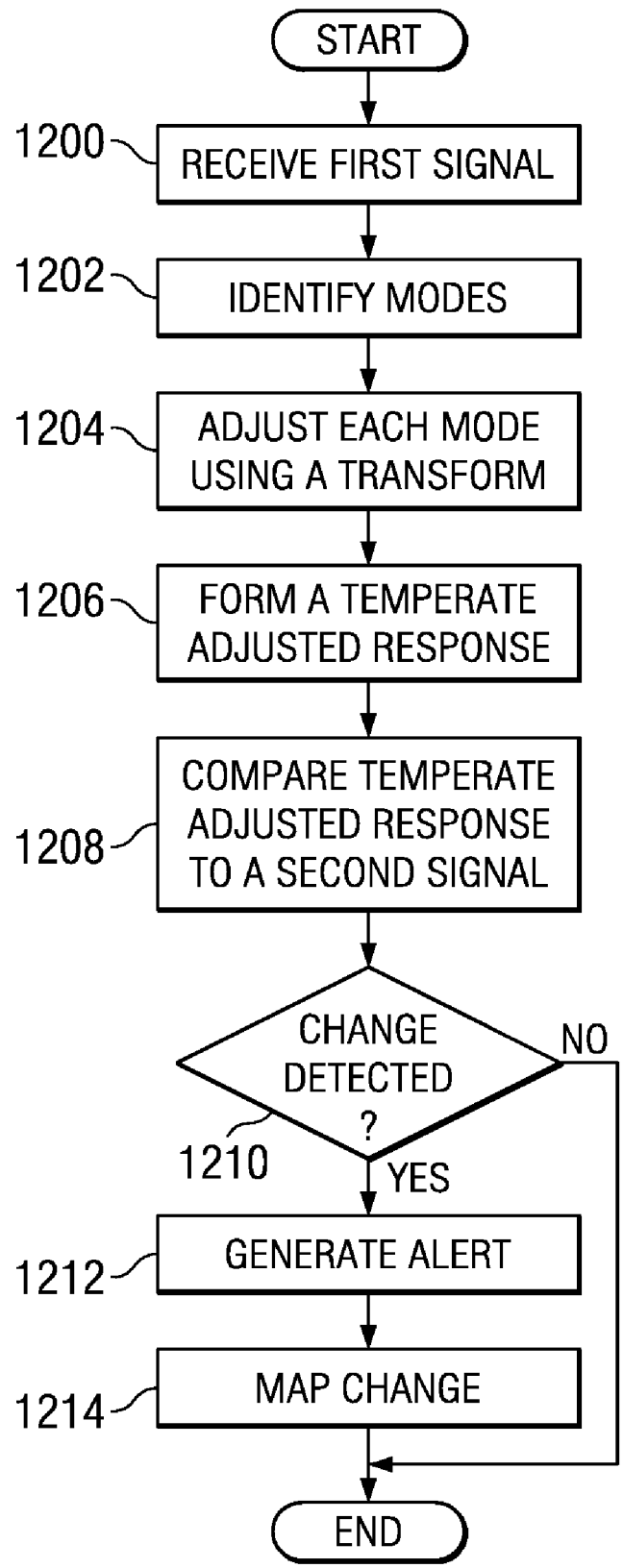
FIG. 12 is a flowchart of a process for monitoring a structure in accordance with an advantageous embodiment.

With reference now to FIG. 12, a flowchart of a process for monitoring a structure is depicted in accordance with an advantageous embodiment. The process illustrated in FIG. 12 may be implemented in a health monitoring system such as, for example, data processing system 600 in FIG. 6.

The process begins by receiving a first signal (operation 1200). The process identifies modes from the first signal (operation 1202). The process adjusts each mode using a transform (operation 1204). Operation 1204 is performed by adjusting each mode individually and separately from other modes with a transform that is designed or selected for that particular mode.

The process forms a temperature adjusted response from the temperature adjusted modes (operation 1206). The process then compares the temperature adjusted response to a second signal (operation 1208).

A determination is made as to whether a change in the structure has been detected by using the comparison (operation 1210). If a change has been detected, an alert is generated (operation 1212) and the change is mapped (operation 1214), with the process terminating thereafter. The alert may be, for example, a message or signal sent to another component or user. Operation 1214 may generate a two-dimensional or three-dimensional map of the structure identifying the position of the detected change. With reference again to operation 1210, if a change is not detected, the process terminates.

The illustration of the process in FIG. 12 is provided as one manner in which a structure may be monitored using the different advantageous embodiments. Of course, other operations in addition to or in place of the ones illustrated may be used. Also, the order of the different operations also may be changed depending on a particular implementation.

For example, the generation of the alert in operation 1212 and the mapping of the change in operation 1214 may be performed in different orders or both operations may be performed simultaneously. In some advantageous embodiments, the first signal may be the response generated during monitoring while the second signal is the baseline response from a prior time. In other advantageous embodiments, the first signal may be the baseline response, while the second signal is the response obtained during the monitoring of the structure.

Figure 13:
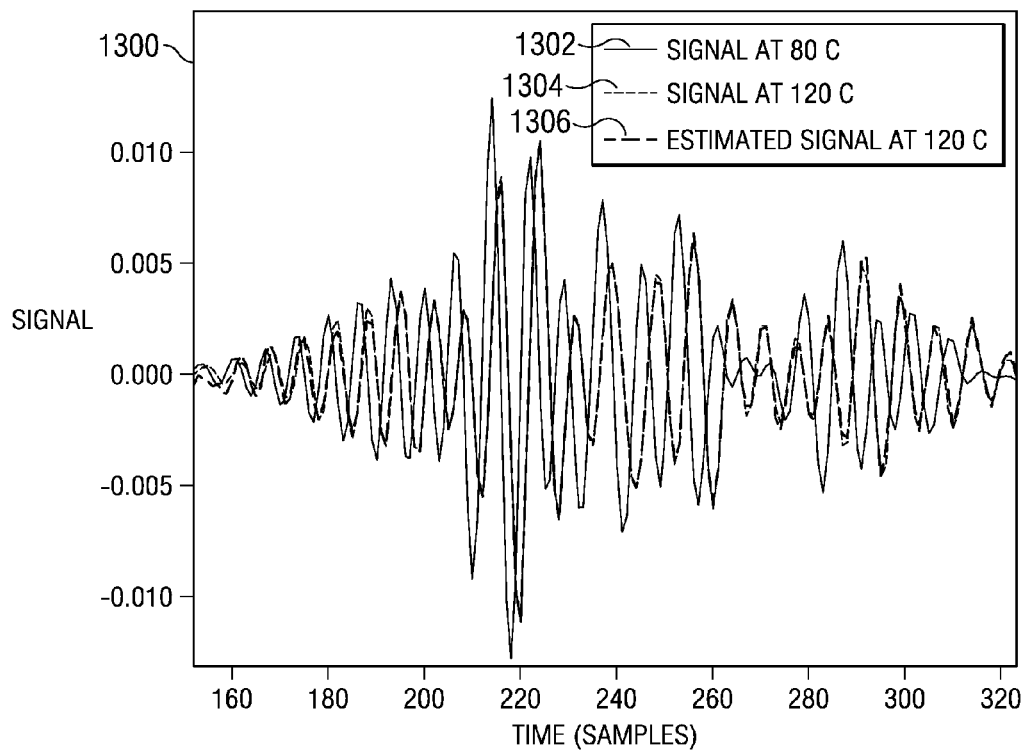
FIG. 13 is a diagram of sensor data showing the effects of temperature on signals in accordance with an advantageous embodiment.

With reference now to FIG. 13, a diagram of sensor data showing the effects of temperature on signals is depicted in accordance with an advantageous embodiment. In graph 1300, the x-axis represents time in samples, while the y-axis represents signal amplitude in volts.

In graph 1300, sensor data is shown for signal 1302, signal 1304, and estimated signal 1306. Signal 1302 is the signal generated for a structure at 80° C., while signal 1304 is a signal generated for a structure at 120° C. Estimated signal 1306 is for a transformation of signal 1302 from 80° F. to 120° F.

In these examples, this data was obtained from tests on a composite panel. This panel was a flat 42-ply composite panel. Graph 1300 shows a representative set of results from the tests. The input signals generating the results shown in graph 1300 were from linear input signals of a limited duration. The signals illustrated in graph 1300 are for a sensor and transmitter pair that is approximately 6 inches apart.

As can be seen from this example, signal 1302 and signal 1304 are different from each other, while estimated signal 1306 matches 1302 fairly closely. The correlation coefficient between signal 1304 and estimated signal 1306 is 0.986 indicating that the compensation performed using advantageous embodiments provided a very good compensation. The correlation coefficient between signal 1302 and signal 1304 is −0.076. This result indicates a very large difference between the two signals even though they were generated using the same transmitter and sensor pair in the same configuration.

Figure 14:
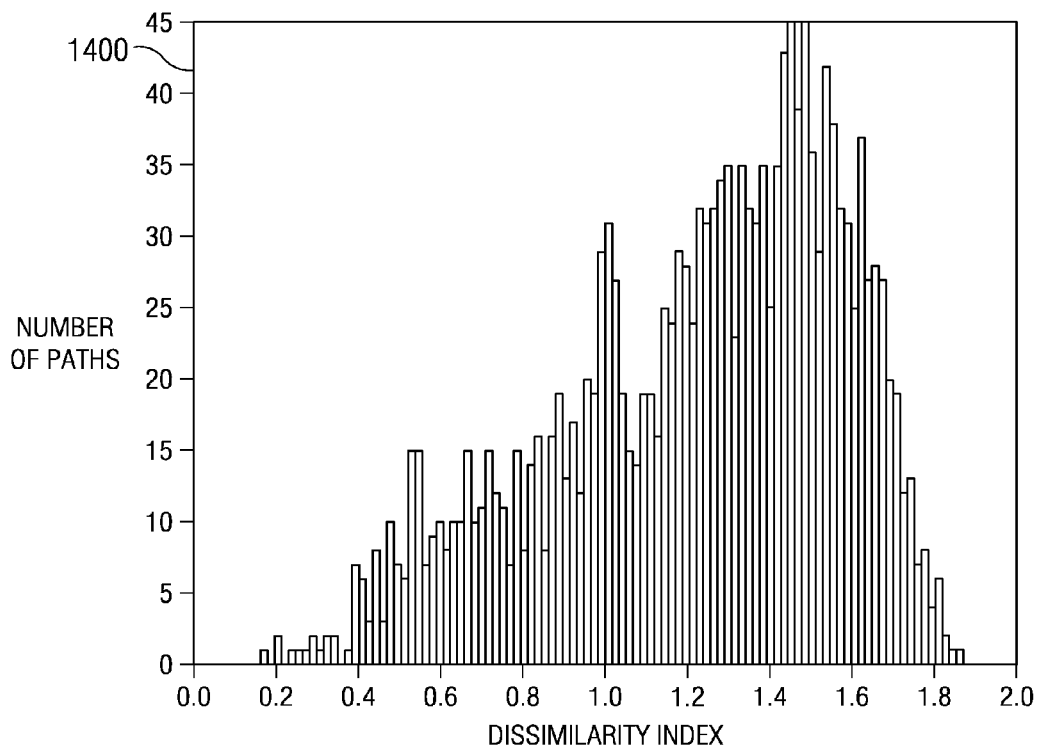
FIG. 14 is a histogram of dissimilarity indices.

With reference now to FIG. 14, a histogram of dissimilarity indices is depicted. A dissimilarity index is a value that may be used to represent a difference between two signals obtained for a structure at different points in time. For example, a dissimilarity index may be assigned based on a difference between a baseline signal and a test signal obtained for a structure. In graph 1400, the x-axis represents dissimilarity index values while the y-axis represents the number of transmitter-sensor pairs for which the dissimilarity index was calculated. In this example, the baseline data was collected at 80° C. and the test data was acquired at 120° C. The comparison was made between these two signals with graph 1400 resulting.

Figure 15:
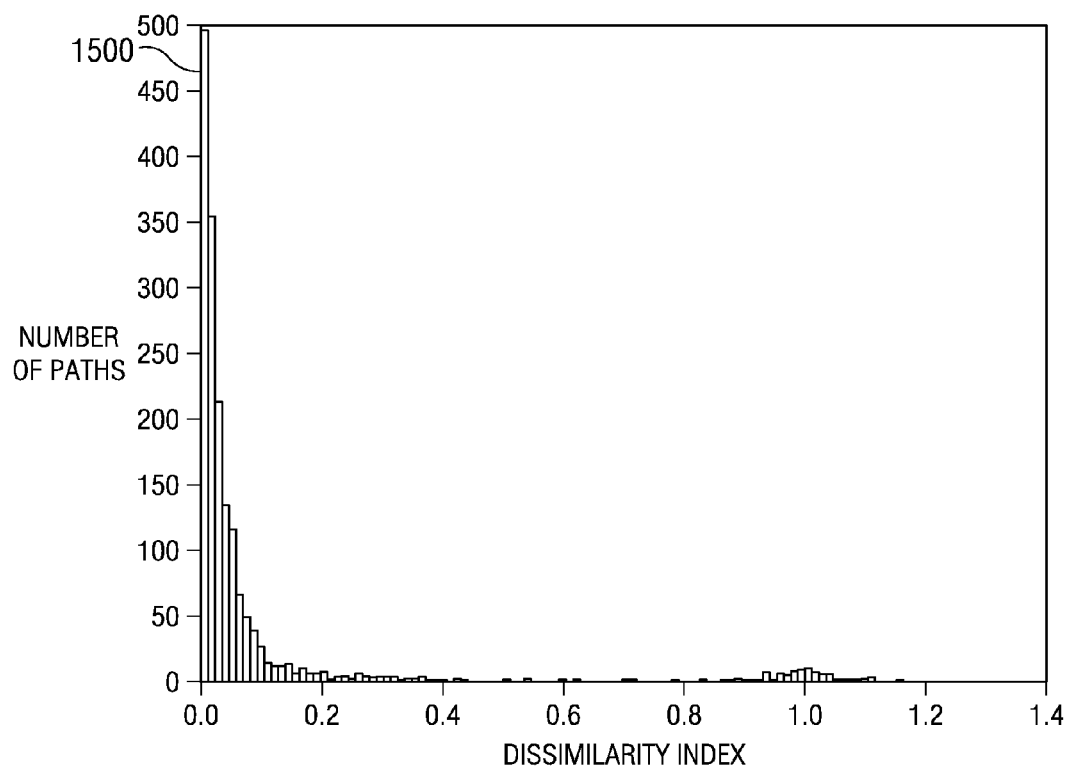
FIG. 15 is a histogram of dissimilarity indices.

With reference now to FIG. 15, a histogram of dissimilarity indices is depicted. In this example, the baseline data and the test data were both acquired at 120° F. In this example, graph 1500 has dissimilarity index values on the x-axis while the y-axis shows the number of paths.

In this example, graph 1500 shows baseline data and test data acquired at 120° F. Graph 1500 identifies dissimilarity indices for the same structure as graph 1400 in FIG. 14. The temperature difference between the baseline signal and the test signal provides varying results with the same structure.

Figure 16:
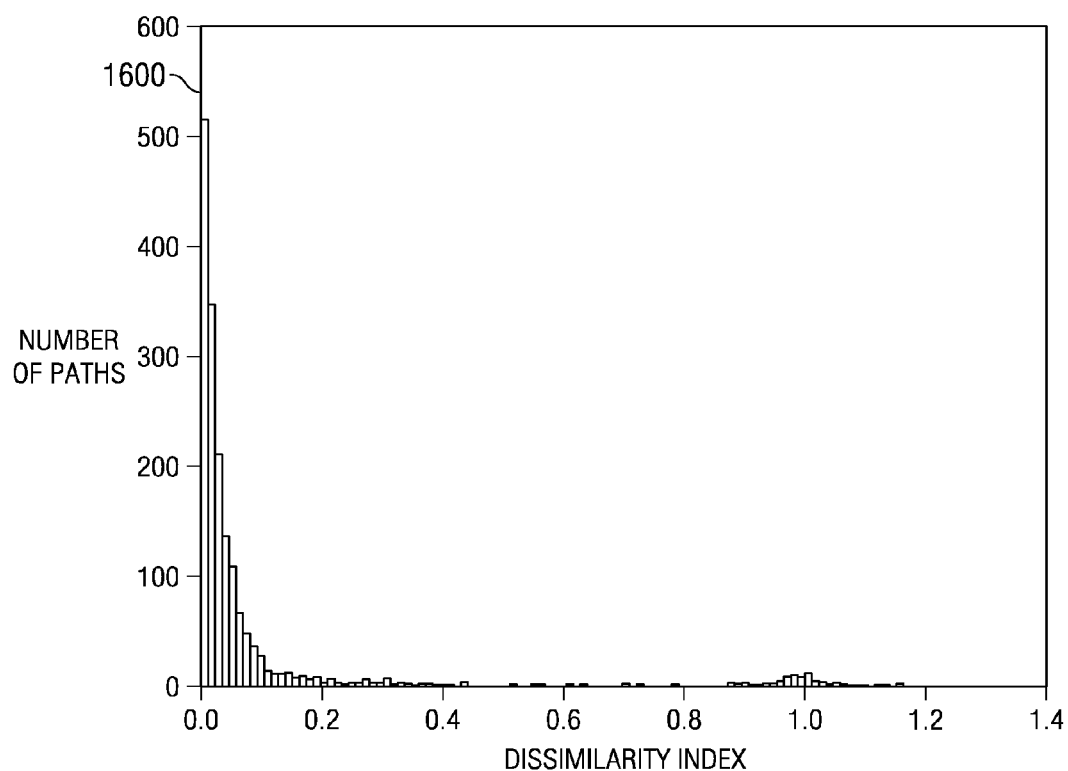
FIG. 16 is a histogram of dissimilarity indices obtained after temperature compensation.

With reference now to FIG. 16, a histogram of dissimilarity indices obtained after temperature compensation is depicted with an advantageous embodiment. In this example, graph 1600 illustrates dissimilarity indices after applying temperature compensation to the baseline data. Graph 1600 appears close to the data illustrated in graph 1500 for data acquired at 120° F. In this example, the dissimilarity index is generated from data in which the baseline data was collected at 80° F. and the subsequent test data was acquired at 120° F. In this example, temperature compensation was performed by applying temperature compensation to the baseline data. As can be seen, this data is much closer to that shown in graph 1500 in FIG. 15.

As can be seen with respect to FIGS. 14-16, the identification of changes is more accurate when temperature compensation is performed using different advantageous embodiments. In this manner, misleading or erroneous results may be reduced or avoided using a health monitoring system according to an advantageous embodiment.

Figure 17:
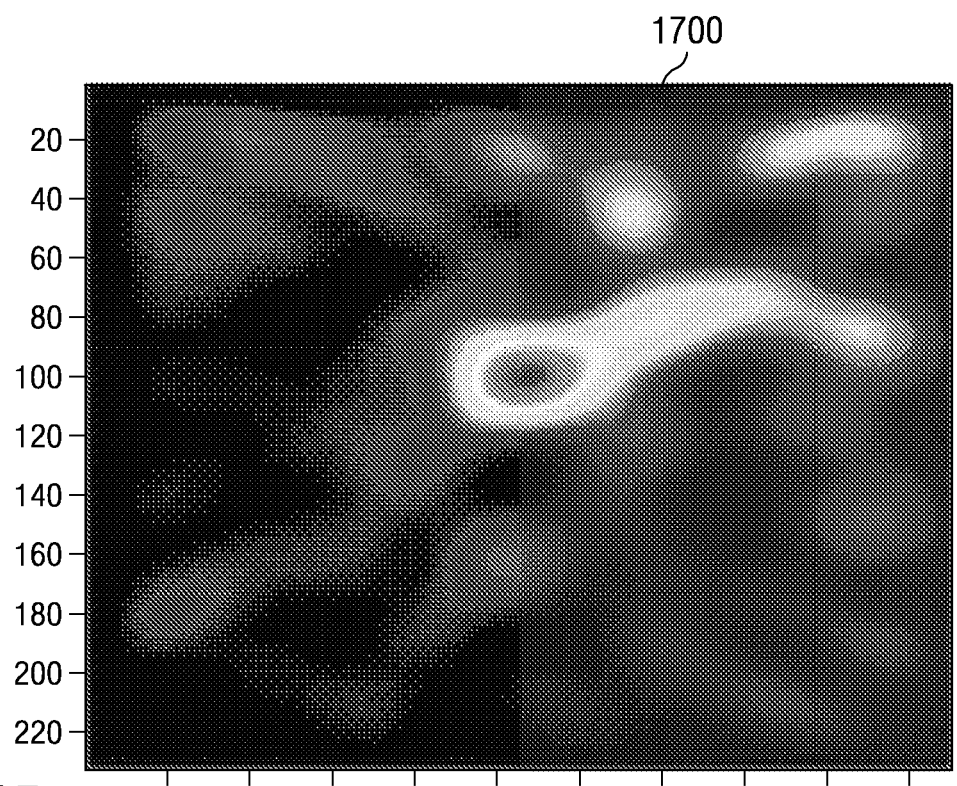
FIG. 17 is an illustrative example of a change map.

FIG. 17 is an example of a change map. Map 1700 is generated with baseline data and test data being collected at 120° F.

Figure 18:
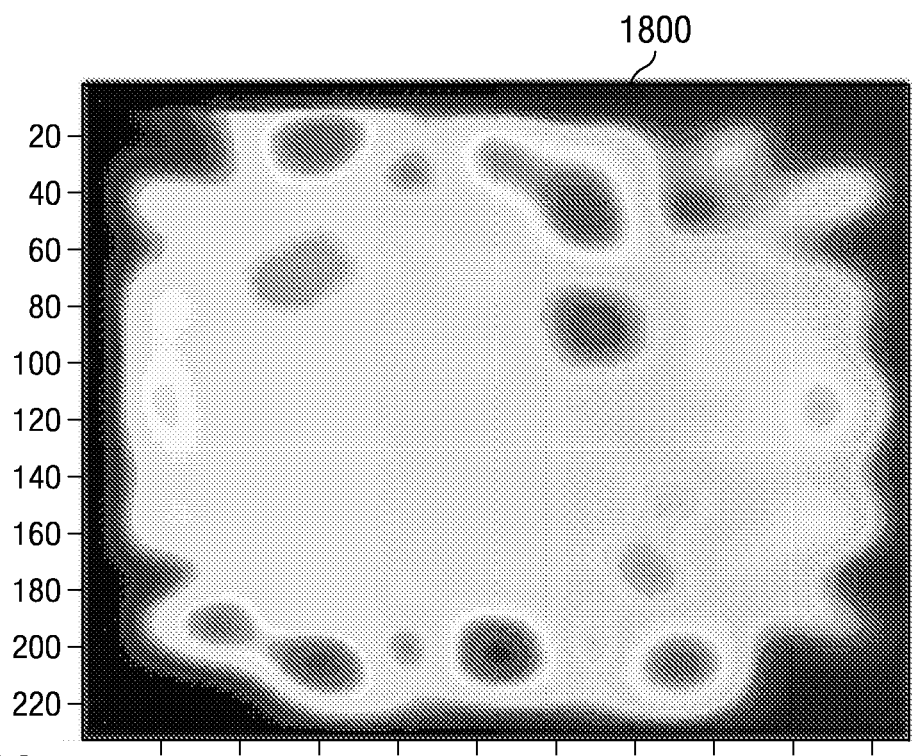
FIG. 18 is a diagram illustrating a change map in accordance with an advantageous embodiment.

With reference now to FIG. 18, a diagram illustrating a change map is depicted. Map 1800 is an example of a change map with baseline data acquired at 80° F. and test data collected at 120° F. As can be seen, the differences between map 1700 and map 1800 are great even though the data was obtained for the same structure. The changes in map 1800 are caused by the uncompensated effects of temperature on the acquired data and does not reflect changes in the structure between the times the baseline and test data were acquired.

Figure 19:
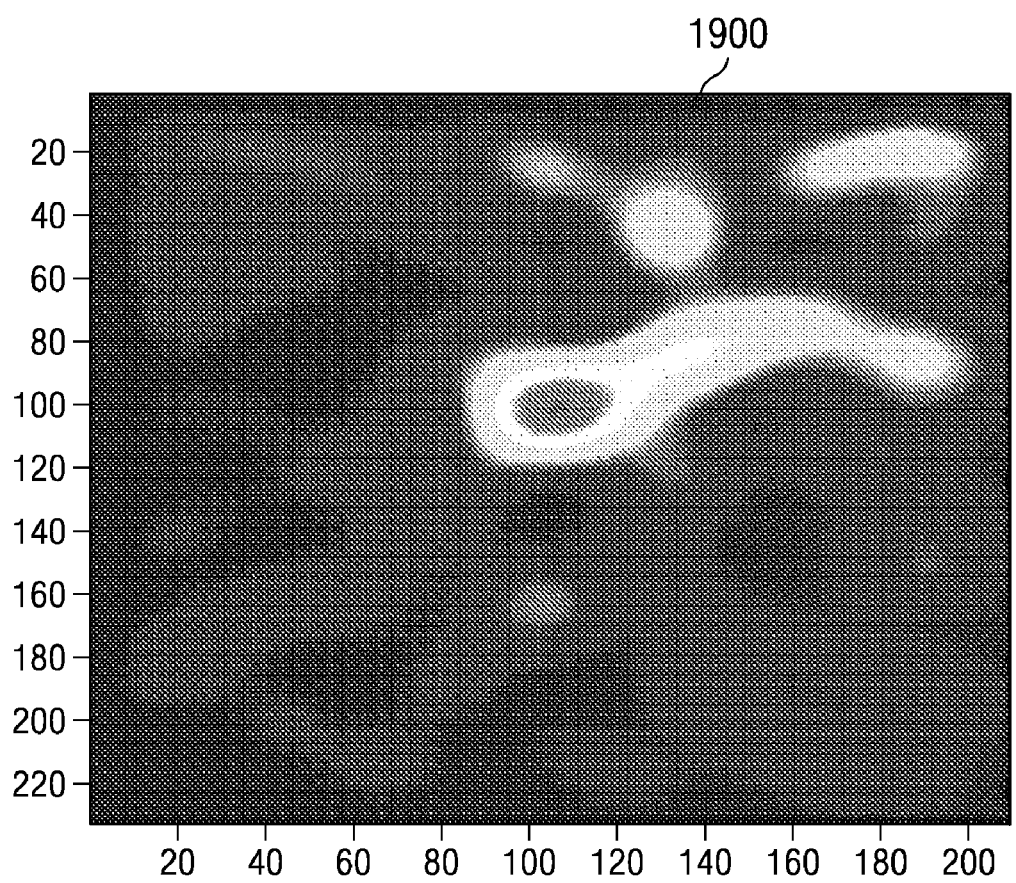
FIG. 19 is an illustrative example of a change map generated after temperature compensation in accordance with an advantageous embodiment.

With reference now to FIG. 19, a change map generated after temperature compensation is depicted in accordance with an advantageous embodiment. In this example, map 1900 is generated after performing temperature compensation for baseline data acquired at 80° F. and test data collected at 120° F. In this example, map 1900 was generated after baseline data was compensated to provide an estimate at 120° F.

As can be seen, map 1700 and map 1900 are very close to each other. In these examples, the maximum difference between map 1700 and map 1900 is a 3 percent of the peak value in map 1700. As can be seen, map 1900 provides a better identification of changes in the structure as compared to identifying changes without compensating for temperature.

Thus, the different advantageous embodiments provide a method and apparatus for monitoring a structure. The different advantageous embodiments identify a plurality of modes for a first response for the structure at a first temperature. Each mode in the plurality of modes is adjusted from the first temperature to the second temperature to form a plurality of temperature adjusted modes.

A temperature adjusted response is formed from the plurality of temperature adjusted modes in which the temperature adjusted response is adjusted to the second temperature from the first temperature. This temperature adjusted response may be compared to a second response obtained at the second temperature. In this manner, identifications of changes in a structure may be determined with more accuracy than other considered mechanisms.

The different advantageous embodiments can take the form of an entirely hardware embodiment, an entirely software embodiment, or an embodiment containing both hardware and software elements. Some embodiments are implemented in software, which includes but is not limited to forms, such as, for example, firmware, resident software, and microcode.

Furthermore, the different embodiments can take the form of a computer program product accessible from a computer-usable or computer-readable medium providing program code for use by or in connection with a computer or any device or system that executes instructions. For the purposes of this disclosure, a computer-usable or computer readable medium can generally be any tangible apparatus that can contain, store, communicate, propagate, or transport the program for use by or in connection with the instruction execution system, apparatus, or device.

The computer usable or computer readable medium can be, for example, without limitation an electronic, magnetic, optical, electromagnetic, infrared, or semiconductor system, or a propagation medium. Non limiting examples of a computer-readable medium include a semiconductor or solid state memory, magnetic tape, a removable computer diskette, a random access memory (RAM), a read-only memory (ROM), a rigid magnetic disk, and an optical disk. Optical disks may include compact disk-read only memory (CD-ROM), compact disk-read/write (CD-R/W) and DVD.

Further, a computer-usable or computer-readable medium may contain or store a computer readable or usable program code such that when the computer readable or usable program code is executed on a computer, the execution of this computer readable or usable program code causes the computer to transmit another computer readable or usable program code over a communications link. This communications link may use a medium that is, for example without limitation, physical or wireless.

A data processing system suitable for storing and/or executing computer readable or computer usable program code will include one or more processors coupled directly or indirectly to memory elements through a communications fabric, such as a system bus. The memory elements may include local memory employed during actual execution of the program code, bulk storage, and cache memories which provide temporary storage of at least some computer readable or computer usable program code to reduce the number of times code may be retrieved from bulk storage during execution of the code.

Input/output or I/O devices can be coupled to the system either directly or through intervening I/O controllers. These devices may include, for example, without limitation to keyboards, touch screen displays, and pointing devices. Different communications adapters may also be coupled to the system to enable the data processing system to become coupled to other data processing systems or remote printers or storage devices through intervening private or public networks. Non-limiting examples are modems and network adapters are just a few of the currently available types of communications adapters.

The description of the different advantageous embodiments has been presented for purposes of illustration and description, and is not intended to be exhaustive or limited to the embodiments in the form disclosed. Many modifications and variations will be apparent to those of ordinary skill in the art.

Further, different advantageous embodiments may provide different advantages as compared to other advantageous embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. A method for monitoring a structure, the method comprising:
    identifying a plurality of modes for a first response for the structure at a first temperature;
    adjusting each mode in the plurality of modes from the first temperature to a second temperature to form a plurality of temperature adjusted modes;
    forming a temperature adjusted response from the plurality of temperature adjusted modes in which the temperature adjusted response is adjusted to the second temperature from the first temperature; and
    comparing the temperature adjusted response to a second response obtained at the second temperature.

2. The method of claim 1 further comprising:
    sending a signal into the structure, wherein the signal causes the first response.

3. The method of claim 2, wherein sending step comprises:
    sending the signal into the structure using a transmitter.

4. The method of claim 3 further comprising:
    receiving the first response using a sensor.

5. The method of claim 4, wherein the transmitter and the sensor are a transducer.

6. The method of claim 1 further comprising:
    determining whether a change has occurred in the structure from comparing the temperature adjusted response to the second response obtained at the second temperature.

7. The method of claim 1, wherein the adjusting step comprises:
    adjusting the each mode in the plurality of modes from the first temperature to the second temperature using a set of transforms to form the plurality of temperature adjusted modes.

8. The method of claim 6 further comprising:
    responsive to a determination that the change has occurred in the structure, mapping the change.

9. The method of claim 1, wherein the structure is selected from one of an aircraft, a building, a dam, a submarine, a spacecraft, a ship, a truck, a tank, a bridge, and a wall.

10. An apparatus comprising:
    a structure having a set of components;
    a set of transmitters physically associated with the set of components, wherein the set of transmitters is capable of sending signals into the set of components;
    a set of sensors physically associated with the set of components, wherein the set of sensors is capable of detecting a response to the signals; and
    a data processing system in communication with the set of transmitters and the set of sensors, wherein the data processing system is capable of identifying a plurality of modes for a first response for the structure at a first temperature; adjusting each mode in the plurality of modes from the first temperature to a second temperature to form a plurality of temperature adjusted modes; forming a temperature adjusted response from the plurality of temperature adjusted modes in which the temperature adjusted response is adjusted to the second temperature from the first temperature; and comparing the temperature adjusted response to a second response obtained at the second temperature.

11. The apparatus of claim 10, wherein the data processing system is capable of causing the set of transmitters to send a signal into the structure, wherein the signal causes the first response and receives the first response using the set of sensors.

12. The apparatus of claim 10, wherein the data processing system is configured to determine whether a change has occurred in the structure from comparing the temperature adjusted response to the second response obtained at the second temperature.

13. The apparatus of claim 12, wherein the data processing system is configured to map the change in response to a determination that the change has occurred in the structure.

14. The apparatus of claim 10, wherein the data processing system is configured to adjust the each mode in the plurality of modes from the first temperature to the second temperature using a set of transforms.

15. The apparatus of claim 10, wherein the set of transmitters and the set of sensors are a set of transducers.

16. The apparatus of claim 10, wherein a transmitter and a sensor in the set of transmitters and the set of sensors are comprised of a single device that transmits a signal in a first mode and then changes to a second mode to detect a response to the signal.

17. A computer program product comprising:
a non-transitory computer recordable storage media;
program code on the computer readable storage media for identifying a plurality of modes for a first response for a structure at a first temperature;
program code on the computer readable storage media for adjusting each mode in the plurality of modes from the first temperature to a second temperature to form a plurality of temperature adjusted modes;
program code on the computer readable storage media for forming a temperature adjusted response from the plurality of temperature adjusted modes in which the temperature adjusted response is adjusted to the second temperature from the first temperature; and
program code on the computer readable storage media for comparing the temperature adjusted response to a second response obtained at the second temperature.

18. The computer program product of claim 17 further comprising:
program code on the computer readable storage media for sending a signal into the structure using a transmitter, wherein the signal causes the first response; and
program code for receiving the first response using a sensor.

19. The computer program product of claim 17 further comprising:
program code on the computer readable storage media for determining whether a change has occurred in the structure from comparing the temperature adjusted response to the second response obtained at the second temperature.

20. The computer program product of claim 17 further comprising:
program code on the computer readable storage media for receiving the first response using a sensor.

21. The method of claim 1 wherein a mode comprises a component of a waveform.

22. The apparatus of claim 10 wherein a mode comprises a component of a waveform.

23. The computer program product of claim 17 wherein a mode comprises a component of a waveform.

* * * * *